(12) United States Patent
Wang et al.

(10) Patent No.: US 6,225,378 B1
(45) Date of Patent: May 1, 2001

(54) TRIAZINE HARDENER AND EPOXY COMPOSITION CONTAINING THE SAME

(75) Inventors: Shin-Shin Wang, Hsinchu; Hung-Chou Kang, Hsin-Chu; Jie-Hwa Ma, Hsinchu; Meng-Song Yin, Hsin-Chu; Se-Tsun Hong, Ilan; Kuo-Yuan Hsu, Miaoli; Kung-Lung Cheng, Hsinchu, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/345,873

(22) Filed: Jul. 1, 1999

(51) Int. Cl.[7] ............................... C08K 3/20; C08L 63/02
(52) U.S. Cl. ......................... 523/454; 523/455; 528/94; 528/118; 544/196; 544/197; 544/198
(58) Field of Search .................. 528/94, 118; 523/454, 523/455; 544/196, 197, 198

(56) References Cited

U.S. PATENT DOCUMENTS

| | | |
|---|---|---|
| 3,755,322 * | 8/1973 | Winter et al. .................. 544/196 |
| 3,963,714 * | 6/1976 | Gerendas et al. .................. 8/177 |
| 4,514,399 * | 4/1985 | Regnier et al. .................. 514/241 |
| 4,670,558 * | 6/1987 | Ebel et al. .................. 544/196 |
| 5,068,309 | 11/1991 | Shimp et al. .................. 528/211 |

FOREIGN PATENT DOCUMENTS

| | | | |
|---|---|---|---|
| 3611420 * | 10/1987 | (DE) . | |
| 19528882 * | 2/1997 | (DE) . | |
| 0 548 970A2 | 6/1993 | (EP) ................ | C07C/261/02 |
| 51-032887 * | 3/1976 | (JP) . | |

OTHER PUBLICATIONS

Makromol. Chem. (1979) p. 2123–2131, 1979.*

* cited by examiner

Primary Examiner—Robert Dawson
Assistant Examiner—D. Aylward
(74) Attorney, Agent, or Firm—Darby & Darby

(57) ABSTRACT

A triazine compound having formula I or formula II:

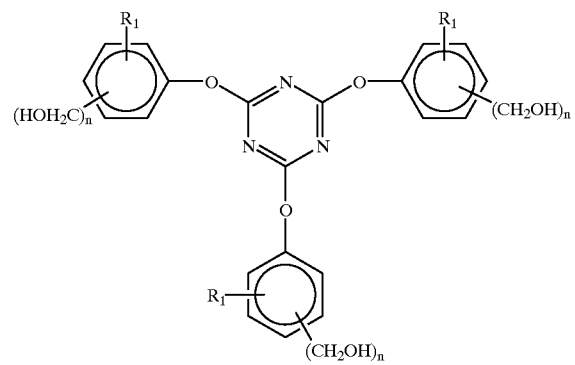

Wherein n is integer from 1 to 5;

R$_1$ is hydrogen, halogen, C$_1$–C$_4$ alkyl, or C$_1$–C$_4$ alkoxyl; and

R$_2$ is aliphatic amine, aliphatic alcohol, alicyclic amine or alicyclic alcohol, and an epoxy resin composition containing the triazine compound. The epoxy resin composition is suitable for the preparation of the structural substrate of printed circuit boards having low dielectric constant.

19 Claims, No Drawings

TRIAZINE HARDENER AND EPOXY COMPOSITION CONTAINING THE SAME

FIELD OF THE INVENTION

The present invention relates to a resin composition to be employed as a substrate of high frequency printed circuit boards. In particular, the invention relates to a novel triazine hardener (curing agent), a resin composition containing the triazine hardener, and a high frequency printed circuit board having low dielectric constant prepared therefrom.

DESCRIPTION OF THE RELATED ART

Epoxy resins, phenolic resins, polyester resins, polyimide resins, BT resins, cyanate ester, PTFE resins and PPE resins have been employed as the resin materials in the preparation of structural substrates of printed circuit boards. It has been disclosed in EPO patent No. 548,970 and U.S. Pat. No. 5,068,309 that the printed circuit boards prepared from dicyanate ester resins have relatively low dielectric constant. However, as the preparation of the dicyanate ester resins requires the use of toxic and high volatile cyanogen halide, epoxy resins are currently being employed in the preparation of structural substrates of printed circuit boards. In the preparation of printed circuit board laminate, epoxy resins are first reacted with a chain extender, and then mixed with hardeners (curing agents), curing promoters and solvents to obtain a mixture, called varnish. The varnish is used to impregnate a woven glass cloth to obtain prepregs. Then the prepregs are laminated with copper clads or foils to form a printed circuit board laminate.

The dielectric constant of epoxy resin-based substrate materials for printed circuit boards currently in use, for example FR-4, are still too high, and thus are not suitable for use in the high frequency applications. Moreover, using epoxy resins as the resin materials of a structural substrate necessitates particular hardeners, which are usually of high cost and have high moisture-absorbing characteristics.

SUMMARY OF THE INVENTION

An object of the invention is to provide a hardener for epoxy resins that is safe and not expensive.

Another object of the invention is to provide an epoxy resin composition for which the substrate material obtained therefrom has lower dielectric constant.

The above objects are achieved by providing a triazine hardener having the formula I or formula II as shown below and an epoxy resin composition containing the triazine hardener.

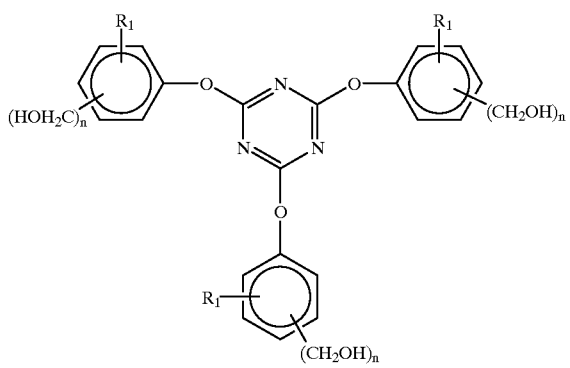

I

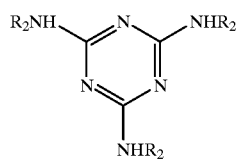

II wherein n is integer from 1 to 5;
  $R_1$ is hydrogen, halogen, $C_1$–$C_4$ alkyl, or $C_1$–$C_4$ alkoxyl; and
  $R_2$ is aliphatic amine, aliphatic alcohol, alicyclic amine or alicyclic alcohol.

DETAILED DESCRIPTION OF THE INVENTION

The trazine hardener of formula I is ether type triazine and is prepared by reacting cyanuric chloride with phenol derivatives as shown in the reaction scheme below.

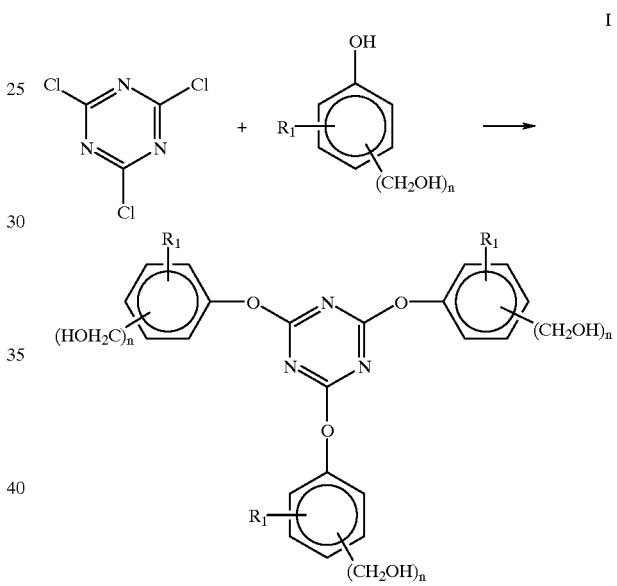

I

The triazine hardener of formula II is an amine type triazine and is prepared by reacting cyanuric chloride with amine derivatives as shown in reaction scheme below.

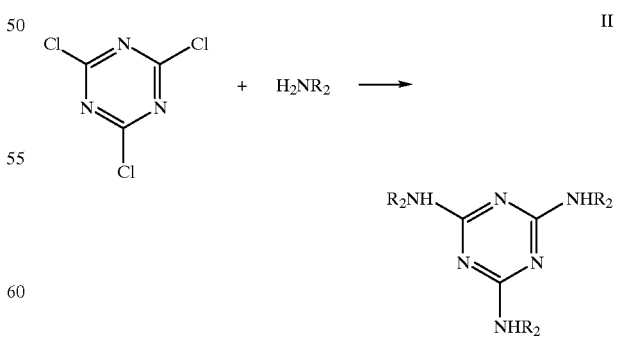

II

The reactant, cyanuric chloride, is nontoxic and nonvolatile, and thus the process of producing the triazine hardener of the invention is safe and environment friendly. Moreover, the triazine hardener of the invention has superior solubility and thus can facilitate the preparation of the resin substrate. In addition, the triazine of the invention has at least 3 active hydrogen in its structure. This can increase the functionality of the epoxy resin, and result in a larger crosslinking density with the epoxy resin, thereby increasing the thermal resistance and mechanical strength of the resultant substrate. The triazine of the invention also has lower dielectric constant (Dk), and thus the printed circuit boards prepared therefrom have relatively low dielectric constant.

The epoxy resin composition of the invention includes epoxy resins, the triazine mentioned above, suitable curing promoters and solvents. The amount of the epoxy resins is 45–95 percent by weight, preferably 60–90, based on the total amount of the composition. The amount of the triazine hardener is such that the ratio between the equivalent of the active hydrogen in the triazine and the equivalent of the epoxide groups of the epoxy resin is about 0.5–1.2, preferably 0.8–1.0.

According to the invention, suitable epoxy resins include but are not limited to bisphenol-A epoxy resin, brominated epoxy resin (bromine content: 10–60 wt %), novolac epoxy resin, multifunctional epoxy resin, aliphatic epoxy resin. Mixture of the above mentioned epoxy resins in a predetermined ratio is also suitable for use. Examples of the epoxy resins are bisphenol A epoxy resin, tetrabromo bisphenol A epoxy resin, tetrabromo bisphenol A polyphenol epoxy resin, ortho-cresol novolac epoxy resin, N,N,N',N'-tetra(2,3-epoxypropyl)-P',P'-methylaniline, N,N-bis(2,3-epoxypropyl)-4-amino-phenylepoxypropyl ether and 4-epoxypropylene-N,N-bisepxoypropylaniline and the like.

According to the invention, suitable curing promoters include but are not limited to tertiary amines, quaternary ammonium salts, imidazoles and boron trifluorideamine complexes. Examples of these curing promoters are triethyl amine HCl complex, triethyl amine HBr complex, triethyl amine, bismethyl aniline, trimethylphenyl ammonium chloride, trimethyl ammonium hydroxide, tetrabutyl ammonium hydroxide, triphenylethyl phosphonium chloride, triphenylethyl phosphonium acetate, tetrabutyl phosphonium iodide and 2-methyl imidazole.

Optionally, the epoxy resin composition of the invention can also include one or more solvents. Examples of the solvents suitable for use in the invention include acetone, methylethyl ketone, toluene, xylene and N,N'-dimethyl formamide. Mixtures of the above-mentioned solvents are also suitable for use.

When the epoxy resin composition is used to prepare the substrate of printed circuit boards, it is mixed with suitable solvents to form varnish. Woven glass fiber clothes are then impregnated with the varnish to give prepregs. The prepregs are then laminated and hot pressed to form epoxy resin substrate laminate. The process of fabricating the substrate laminate is familiar to those skilled in this art and thus the detailed description is omitted. The epoxy resin substrates fabricated by using the epoxy resin composition of the invention have a dielectric constant of about 4.0.

The following examples are intended to demonstrate the invention more fully without acting as a limitation upon its scope, since numerous modifications and variations will be apparent to those skilled in this art.

EXAMPLE 1

Preparation of 2,4,6-tri(6'-hydroxy-1'-hexylamino) triazine, formula II, $R_2=(CH_2)_6OH$)

0.09 g (0.005 mole) of cyanuric chloride, 7.95 g of sodium carbonate, 1.75 g (0.015 mole) of 6-amino-1-hexanol, 10 ml of n-heptane and 10 ml of methanol were placed in a 50 ml two-necked flask, and agitated at room temperature for 30 minutes. Solvent was then evacuated and 30 ml of water was added to the flask and agitated. After filtration, 1.6 g (0.038 mole) of the title compound in white was obtained. The yield was 75%.

Data of spectra; $^1$HNMR(DMSO-d6):δ 7.8(br,3H), 4.4(s,3H), 3.5(t,2H),3.3(m,2H),1.59(m,2H),1.53(m,2H), 1.38(m,2H), 1.37(m,2H). $^{13}$CNMR (DNSO-$d_6$):δ 165.3, 60.7, 39.9, 32.5, 28.8, 26.3, 25.2. MS (m/e): 427 (M+1).

EXAMPLE 2

Preparation of N,N',N"-2,4,6-tri(5-amino-1,3,3-trimethyl-cyclohexane) methylamino-1,3,5-triazine, formula II,

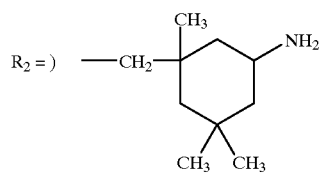

49 g of cyanuric chloride, 800 ml of n-heptane and 275 ml of methanol were placed in a four-necked flask, and the reaction temperature was lowered to 10° C. 136 g of isophorone diamine was then added in the resulting solution dropwise within 1 hour and allowed to react overnight. The pH of the reaction solution was then adjusted to 12 and 1500 ml of water was added and agitated to obtain a white solid precipitate. The white solid precipitate was filtrated and dried to give 143.8 g of the title compound. The yield was 92%.

Data of spectra; $^1$HNMR(CD$_3$OD):δ 1.35 (br,11H), 1.54 (br,4H), 2.05(br,3H), $^{13}$CNMR(CD$_3$OD):δ 179.2, 55, 45.2, 44.6, 37.9, 35.7, 32.8,30.6, 28.3, 24.3. MS(m/e): 586(M−1).

EXAMPLE 3

Preparation of C,C',C"-(4,4',4"-(1,3,5)triazine-2,4,6-triyltrioxytirphenyl) tris-methanol; formula I, n=1, $R_1$=H)

151 g of p-hydroxy benzaldehyde, 280 g of sodium carbonate, and 2.8 liter of ethyl acetate were charged into a 3 liter four-necked flask equipped with a mechanical agitator, heated to reflux, and dehydrated with 4A° molecular sieve for 2 hours. After cooling, 70 g of cyanuric chloride was added and the solution heated again to reflux for 5 hours. The resulting organic layer solution was then poured into an extraction bottle while it is hot. To the solid in the reaction flask was added 1.4 liter of ethyl acetate and heated to 75° C., and then poured into the extraction bottle. The procedure was repeated once. The organic layer solution was collected and extracted with hot sodium carbonate solution once and again extracted with hot water. The organic layer was then decolorized, subjected to filtration, concentrated and dried to give 163.1 g of a white solid (yield: 97.2%, water content: 1.5%).

38.15 g of the white solid and 750 ml of tetrahydro furan was added to a 2 liter three-necked flask, and the reaction mixture was lowered to 4° C. 8.55 g of sodium borohydide was added and allowed to react for 5 hours. 150 ml of water was added and the pH value of the reaction solution was adjusted to 8–8.5 by using diluted phosphoric acid. The reaction solution was then poured in an extraction bottle. The organic layer was concentrated and 1 liter of water was added to the obtained solid, agitated, filtered and dried to give 29.0 g of the title compound. The yield was 75%.

Data of spectra; $^1$HNMR(DMSO-$d_6$):δ 7.25 (d,d,12H), 5.2(s,3H), 4.49 (s,6H). $^{13}$C NMR (DMSO-$d_6$):δ 173, 150, 140, 127.5, 121, 62.3. MS (m/e): 448 (M−1)

EXAMPLE 4

Preparation of C,C',C"-(3,3',3"-methoxy-4,4',4"-(1, 3,5) triazine-2,4,6-triyltrioxytirphenyl)tris-methanol; formula I, n=1, $R_1$=OCH$_3$)

3 g of cyanuric chloride, 100 ml of N,N-dimethylformamide, 4.3 g of pyridine and 8.1 g of 3-,ethoxy-4-hydroxy benzaldehyde were placed in a 250 ml three-necked flask, and the reaction temperature was heated to 84° C.for 3 hours. After cooling, the reaction solution was poured into 1 liter of water, filtered to obtain a solid. The obtained solid was washed with aqueous solution of sodium carbonate, subjected to filtration, dried to give 6.9 g of a white. The yield was 80%.

1 g of the white solid and 10 ml of ethanol were added to a 25 ml three-necked flask, and the reaction mixture was cooled to 5° C. 0.2 g of powdered sodium borohydride was added and allowed to react at room temperature overnight. Water was added to terminate the reaction. The ethanol was concentrated and removed. Tetrahydrofuran and water were added to the reaction solution to extract. The obtained organic layer was concentrated, and the obtained solid was washed and purified with methanol to give 0.5 g of the title compound as a milk white solid. The yield was 50%.

Data of spectra; $^1$HNMR(CD$_3$OD):δ 7 (m, 9H), 4.67(s, 6H), 3.8 (s,9H) $^{13}$C NMR (CD$_3$OD):δ 175.4, 152.8, 142.7, 141.4, 123.2, 120, 112.6, 65.2, 56.7 MS (m/e): 538 (M−1)

EXAMPLE 5

20 g of the triazine compound obtained in Example 3 was dissolved in a mixed solvent of 80 g of dimethylformamide and 22 g of actone. 105 g of brominated epoxy resin/ bisphenol A epoxy resin (Epon 1124-A-80/Epon 1004=5/1) was then added and the mixture was mixed intensively. Then 0.15 g of 2-methyl imidiazole (catalyst, 2-MI) was added to a varnish. The varnish was used to impregnate 7628 glass cloth to give 0.20 mm thick prepregs. 4 sheets of prepregs were stacked and hot pressed to obtain 0.8 mm thick laminate. The hot pressing conditions were as follows: pressing pressure:J 35–50 kg/cm$^2$, mold temperature: 180° C., curing time: 40–60 minutes. The resin content of the obtained laminate was 48.5%, and the measured dielectric constant (Dk) was 4.00 (1 MHz).

EXAMPLE 6

15 g of the triazine compound obtained in Example 2 was dissolved in a mixed solvent of 33 g of dimethylformamide, 28 g of actone and 15 g of methanol. 100 g of brominated epoxy resin (Epon 1124-A-80) was then added and the mixture was mixed intensively. Then 0.75 g of 2-methyl imidiazole (catalyst, 2-MI) was added to give a varnish. The varnish was used to impregnate 7628 glass cloth to give 0.20 mm thick prepregs. 4 sheets of prepregs were stacked and hot pressed to obtain 0.8 mm thick laminate. The hot pressing conditions were as follows: pressing pressure: 35–50 kg/cm$^2$, mold temperature: 180° C., curing time: 40–60 minutes. The resin content of the obtained laminate was 43.2%, and the measured dielectric constant (Dk) was 4.00 (1 MHz).

COMPARATIVE EXAMPLE 15 g of dicyandiamide was dissolved in a mixed solvent of 27.5 g of dimethylformamide and 30 g of actone. 100 g of brominated epoxy resin (Epon 1124-A-80) was then added and the mixture was mixed intensively. Then 0.2 g of benzyl dimethyl amine(catalyst) was added to a give a varnish. The varnish was used to impregnate 7628 glass cloth to give 0.20 mm thick prepregs. 10 sheets of prepregs were stacked and hot pressed to obtain 2.0 mm thick laminate. The hot pressing conditions were as follows: pressing pressure: 35–50 kg/cm$^2$, mold temperature: 180° C., curing time: 60 minutes. The resin content of the obtained laminate was 41.1%, and the measured dielectric constant (Dk) was 4.61 (1 MHz).

What is claimed is:

1. A triazine compound having formula I or formula II:

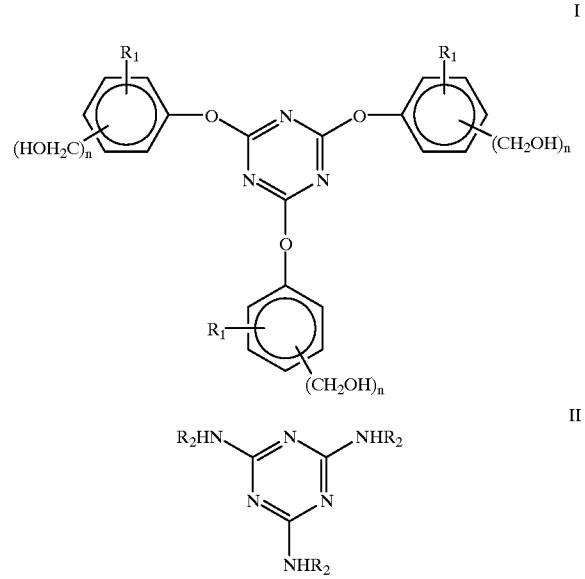

wherein n is an integer from 1 to 5;

$R_1$ is hydrogen, halogen, $C_2$–$C_4$ alkyl, or $C_1$–$C_4$ alkoxyl; and $R_2$ is $C_1$–$C_6$ aliphatic alcohol, $C_{5-6}$ alicyclic amine or $C_{5-6}$ alicyclic alcohol.

2. The triazine as claimed in claim 1, having the formula I wherein $R_1$ is hydrogen and n is 1.

3. The triazine as claimed in claim 1, having the formula I wherein $R_1$ is methoxy and n is 1.

4. The triazine as claimed in claim 1, having the formula II wherein $R_2$ is —(CH$_2$)$_6$OH.

5. The triazine as claimed in claim 1, having the formula II wherein $R_2$ is.

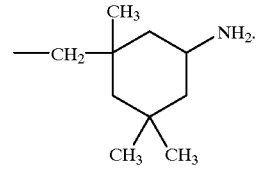

6. An epoxy resin composition comprising:
(a) 45–95 percent by weight of an epoxy resin; and (b) a triazine curing agent having formula I or formula II:

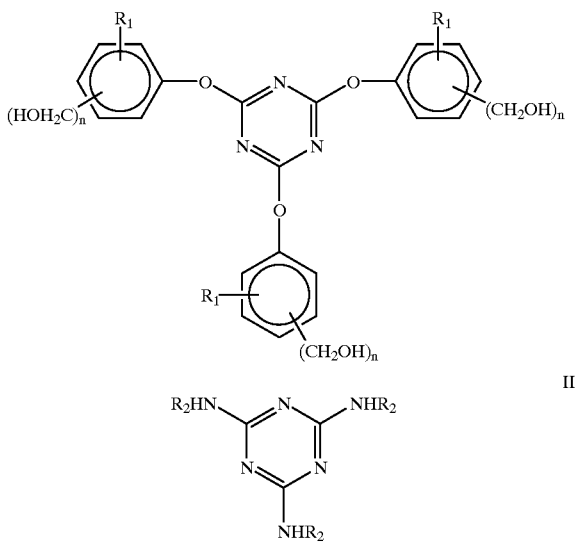

wherein $R_1$ is hydrogen, halogen, $C_{1-4}$ alkyl, or $C_{1-4}$ alkoxyl; and
$R_2$ is $C_{1-6}$ aliphatic amine, $C_{1-6}$ aliphatic alcohol, $C_{5-6}$ alicyclic amine or $C_{5-6}$ alicyclic alcohol; and
(c) 0.001–0.5 percent by weight of a curing promoter;
wherein the ratio between the equivalent of the active hydrogen in said triazine curing agent and the equivalent of the epoxide groups of said epoxy resin is about 0.5–1.2.

7. The epoxy resin composition as claimed in claim 6, wherein said epoxy resin is selected from the group consisting of bisphenol-A epoxy resin, brominated epoxy resin, novolac epoxy resin, multifunctional epoxy resin, aliphatic epoxy resin and mixtures thereof.

8. The epoxy resin composition as claimed in claim 7, wherein said epoxy resin is brominated epoxy resin and the bromine content is 10–60 percent by weight.

9. The epoxy resin composition as claimed in claim 6, wherein the weight ratio between said epoxy resin and the total of the composition is 60–90%.

10. The epoxy resin composition as claimed in claim 6, wherein said tirazine curing agent has a structure of formula I and $R_1$ is hydrogen and n is 1.

11. The epoxy resin composition as claimed in claim 6, wherein said triazine curing agent has a structure of formula I and $R_1$ is methoxy and n is 1.

12. The epoxy resin composition as claimed in claim 6, wherein said triazine curing agent has a structure of formula II and $R_2$ is $(CH_2)_6OH$.

13. The epoxy resin composition as claimed in claim 6, wherein said triazine curing agent has a structure of formula II and $R_2$ is.

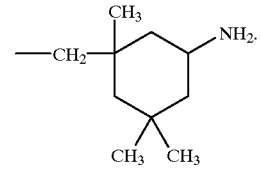

14. The epoxy resin composition as claimed in claim 6, wherein the ratio between the equivalent of the active hydrogen in said triazine curing agent and the equivalent of the epoxide groups of said epoxy resin is about 0.8–1.0.

15. The epoxy resin composition as claimed in claim 6, wherein said curing promoter is selected from the group consisting of tertiary amines, quaternary ammonium salts, imidazoles and boron trifluorideamine complexes.

16. The epoxy resin composition as claimed in claim 15 wherein said curing promoter is 2-methyl imidazole or dimethy aniline.

17. The epoxy resin composition as claimed in claim 6, wherein the weight ratio between said curing promoter and the total of the composition is 0.05–0.25%.

18. The epoxy resin composition as claimed in claim 6, further comprising a solvent.

19. The epoxy resin composition as claimed in claim 18, wherein said solvent is selected from the group consisting of acetone, methyethyl ketone, toluene, xylene, N,N-dimethyl formamide and mixtures thereof.

* * * * *